(12) United States Patent  
Choudhury et al.

(10) Patent No.: US 8,597,216 B2  
(45) Date of Patent: Dec. 3, 2013

(54) ERGONOMIC ARM SLING

(76) Inventors: Sambhu N. Choudhury, Cincinnati, OH (US); Sean M. Lynch, Cincinnati, OH (US); Arturo David Sanchez, Lebanon, OH (US)

( * ) Notice: Subject to any disclaimer, the term of this patent is extended or adjusted under 35 U.S.C. 154(b) by 936 days.

(21) Appl. No.: 12/019,983

(22) Filed: Jan. 25, 2008

(65) Prior Publication Data

US 2009/0192424 A1    Jul. 30, 2009

(51) Int. Cl.  
*A61F 5/00*     (2006.01)

(52) U.S. Cl.  
USPC ............................................................ 602/4

(58) Field of Classification Search  
USPC ............ 602/60, 62, 20, 3–4, 12, 61; 128/874, 128/878, 875, 876, 846; 224/150, 913; 24/31 V, 182  
See application file for complete search history.

(56) References Cited

U.S. PATENT DOCUMENTS

| | | |
|---|---|---|
| 4,355,635 A | 10/1982 | Bihl et al. |
| 4,372,301 A | 2/1983 | Hubbard et al. |
| 4,986,266 A | 1/1991 | Lindemann |
| 5,095,894 A * | 3/1992 | Marble ............................ 602/20 |
| 5,569,172 A | 10/1996 | Padden et al. |
| 5,628,725 A | 5/1997 | Ostergard |
| 6,030,354 A * | 2/2000 | Lakusiewicz ...................... 602/4 |
| 6,453,904 B1 | 9/2002 | Wilson et al. |
| 6,659,971 B2 | 12/2003 | Gaylord |
| 7,037,281 B1 | 5/2006 | Jeffrey et al. |
| 7,189,213 B1 | 3/2007 | Weber |
| 2006/0289018 A1* | 12/2006 | Richard ......................... 128/878 |
| 2007/0043311 A1* | 2/2007 | Jaggan-Vince .................... 602/4 |

* cited by examiner

*Primary Examiner* — Patricia Bianco  
*Assistant Examiner* — Ophelia A Hawthorne  
(74) *Attorney, Agent, or Firm* — Jenei LLC

(57) ABSTRACT

The present invention includes an ergonomic arm sling and method for using the same. The ergonomic arm sling includes a two-piece system that can be used by placing the affected arm into a pouch and securing it with a pouch strap and attaching it to a second portion which is worn around the user's torso. The two pieces can be attached through a connecting means, but are otherwise unattached. The torso portion of the ergonomic arm sling includes a long strip with an opening in the middle such that an unaffected arm can be placed through. Once the end of the strip are connected around the torso, the shoulder of the unaffected arm can bear the weight of the affected arm.

20 Claims, 6 Drawing Sheets

ERGONOMIC ARM SLING

CROSS-REFERENCE TO RELATED APPLICATION

Not applicable.

STATEMENT REGARDING FEDERALLY SPONSORED RESEARCH

Not applicable.

NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND ON THE INVENTION

1. Field of the Invention

The present invention relates generally to an arm sling, more particularly the invention relates to an arm sling that shifts a load away from an individual's neck to a shoulder connected to an individual's unaffected arm.

2. Description of the Related Art

Prior art in the field of arm support includes many different forms of slings. Most of these slings do not distribute the weight of the arm and sometimes a cast equally on both shoulders. Typically they have a strap over the opposite shoulder from the injured or inoperative arm. These single strap devices tend to place an unwanted pressure against the side of the neck.

Further, many of the slings in the prior art involve one piece that provides for the arm support of the affected arm and a means for attachment to one or both shoulders. Because these slings are typically one continuous series of straps, they may be difficult for a user, especially one with an injured arm, to put on and take off easily.

Thus, it is highly desirable to have a means for supporting an arm that balances the weight of an affected arm, avoids placing any unwanted pressure on a user's neck, and allows a user to wear with little difficulty.

SUMMARY

The various exemplary embodiments of the present invention include a sling for supporting a human arm. The sling is comprised of a front strip having a higher part and a base part and capable of extending across a front of a torso. The sling is further comprised of a back strip having a higher part and a base part and capable of extending across a back of a person. The base part of said back strip is capable of connecting with said base part of said front strip by a first connecting means under a shoulder connected to an affected arm. The sling is also comprised of an upper strip connecting a first portion of said higher part of said front strip and a first portion of said higher part of said back strip and supported by a shoulder connected to an unaffected arm. The sling is also comprised of a lower strip connecting both a second portion of said higher part of said front strip and a second portion of said higher part of said back strip and supported by a side of a torso under said shoulder connected to said unaffected arm. The lower strip defines an opening along with said front strip, said back strip, and said upper strip such that said unaffected arm can fit through. The sling is also comprised of a detachable pouch having an exterior side, an interior side, an anterior side, and a posterior side, wherein said exterior side of said pouch is capable of connecting with said front strip by a second connecting means. The pouch is otherwise unconnected to said front strip, said back strip, said upper strip, or said lower strip, and said pouch substantially covers and supports a forearm of said affected arm.

The various exemplary embodiments of the present invention include a method for supporting an affected arm. The method is comprised of placing an unaffected arm through an opening on an arm sling, wherein said arm sling is comprised of a front strip having a higher part and a base part and capable of extending across a front of a torso. The sling is also comprised of a back strip having a higher part and a base part and capable of extending across a back of a person. The base part of said back strip is capable of connecting with said base part of said front strip by a first connecting means under a shoulder connected to an affected arm. The sling is also comprised of an upper strip connecting a first portion of said higher part of said front strip and a first portion of said higher part of said back strip and supported by a shoulder connected to an unaffected arm. The sling is also comprised of a lower strip connecting both a second portion of said higher part of said front strip and a second portion of said higher part of said back strip and supported by a side of a torso under said shoulder connected to said unaffected arm. The lower strip defines an opening along with said front strip, said back strip, and said upper strip such that said unaffected arm can fit through. The sling is also comprised of a detachable pouch having an exterior side, an interior side, an anterior side, and a posterior side, wherein said exterior side of said pouch is capable of connecting with said front strip by a second connecting means. The pouch is otherwise unconnected to said front strip, said back strip, said upper strip, or said lower strip, and said pouch substantially covers and supports a forearm of said affected arm. The method is also comprised of placing a forearm of said affected arm into said pouch and connecting said exterior side of said pouch to said front strip such that said pouch is substantially supported.

BRIEF DESCRIPTION OF THE DRAWINGS

The various exemplary embodiments of the present invention, which will become more apparent as the description proceeds, are described in the following detailed description in conjunction with the accompanying drawings, in which.

DESCRIPTION OF THE REFERENCED MATERIAL

Figure 1:
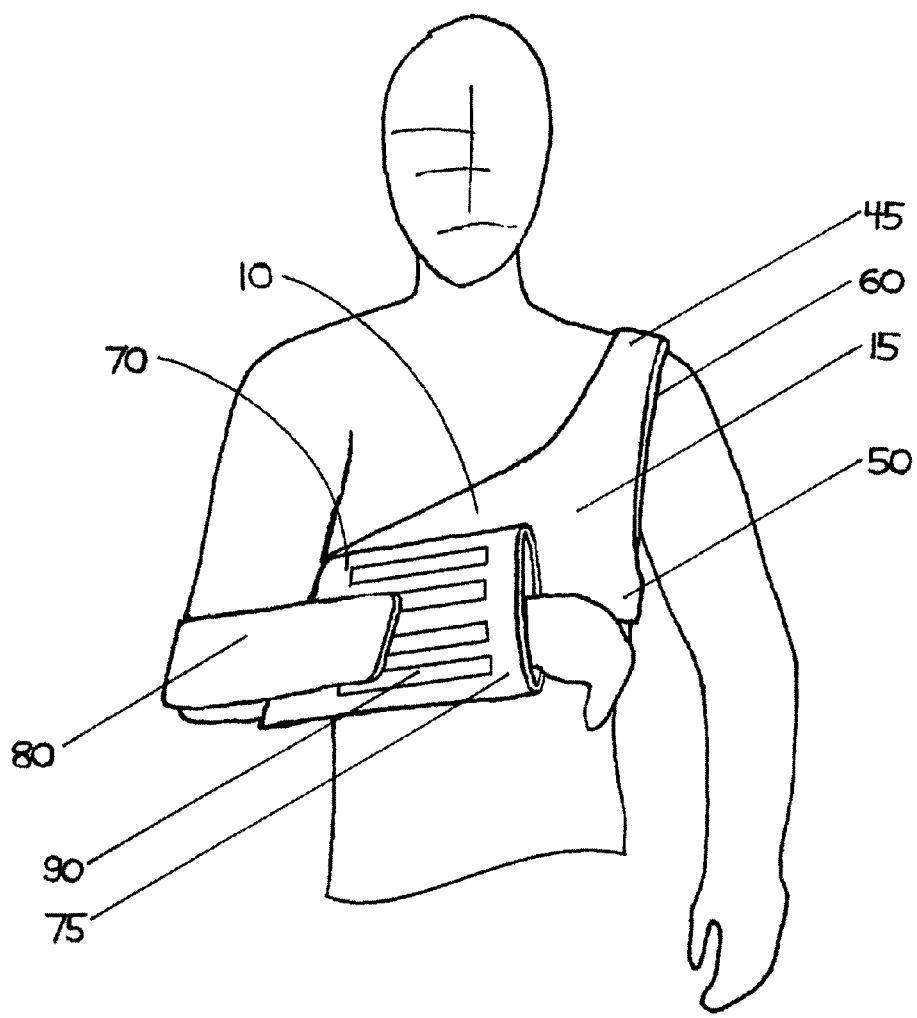
FIG. 1 is an illustration of a front view of an exemplary embodiment of the present invention.

In reference to the drawings, similar reference characters denote similar elements throughout all the drawings. The following is a list of the reference characters and associated element:

10 front strip
15 higher part of said front strip
20 base part of said front strip
30 back strip
35 higher part of said back strip
40 base part of said back strip
45 upper strip
50 lower strip
60 opening
70 pouch
75 exterior side
80 pouch strap
90 hook and fastener strips

DETAILED DESCRIPTION

The drawings show for purposes of further illustration and understanding, that the various exemplary embodiments of the present invention include a sling for supporting a human arm. Although the embodiments as shown in the illustrations display a sling for supporting a right arm, embodiments of the present invention are also capable of supporting a left arm. For example, the present invention can be adapted to support a right arm or a left arm as exemplary embodiments of the present invention are reversible.

FIG. 1 displays a front view of an exemplary embodiment of the present invention as it can be worn. This view shows an affected arm held in a pouch 70 which is supported at an elbow by a pouch strap 80. The pouch 70 and pouch strap 80 compose a first portion of the ergonomic arm sling of the present invention and is releasably attachable to a second portion of the sling that is substantially attached to a torso. In a preferred embodiment, and as shown in FIG. 1, a front strip 10 of the sling is substantially positioned over a chest area. In a preferred embodiment, an upper strip 45, connected to a first portion of a higher part of said front strip 15, is supported by a shoulder connected to an unaffected arm. Also in a preferred embodiment, a lower strip 50 is also connected to a second portion of a higher part of said front strip 15 and wraps around the torso underneath the unaffected arm.

Figure 2:
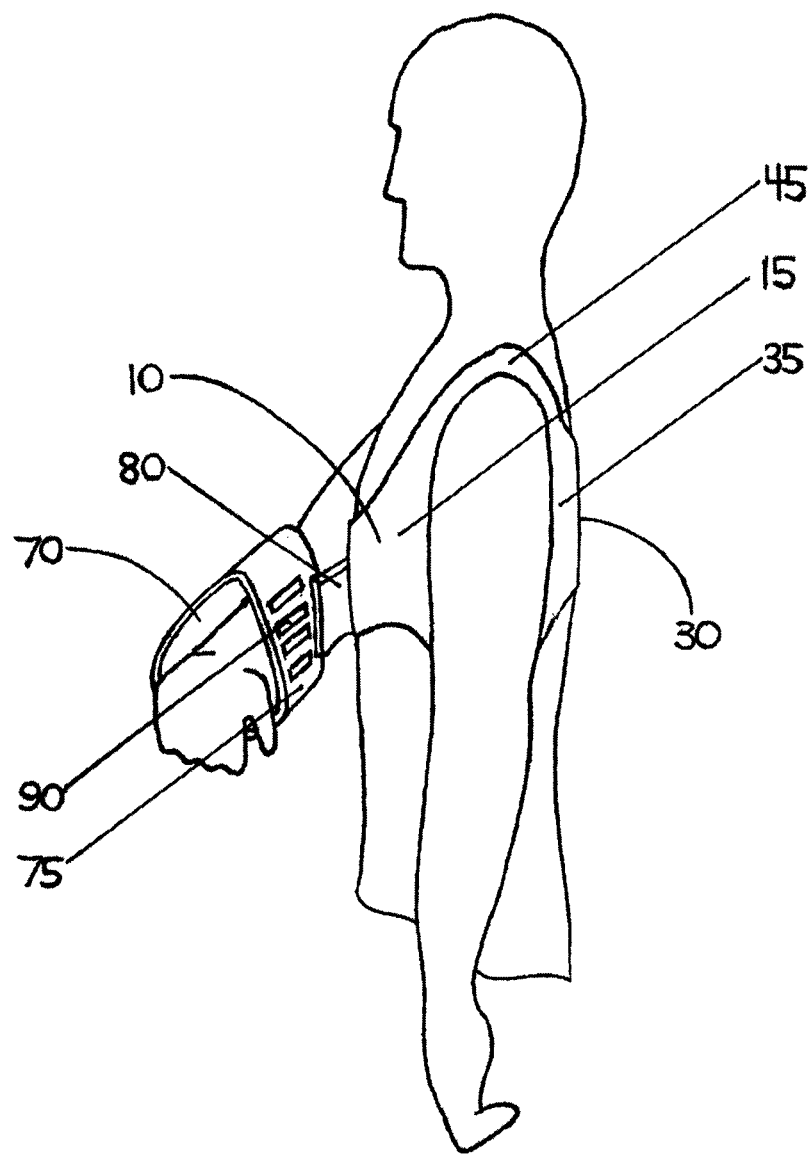
FIG. 2 is an illustration of a side view of an exemplary embodiment of the present invention.
Figure 3:
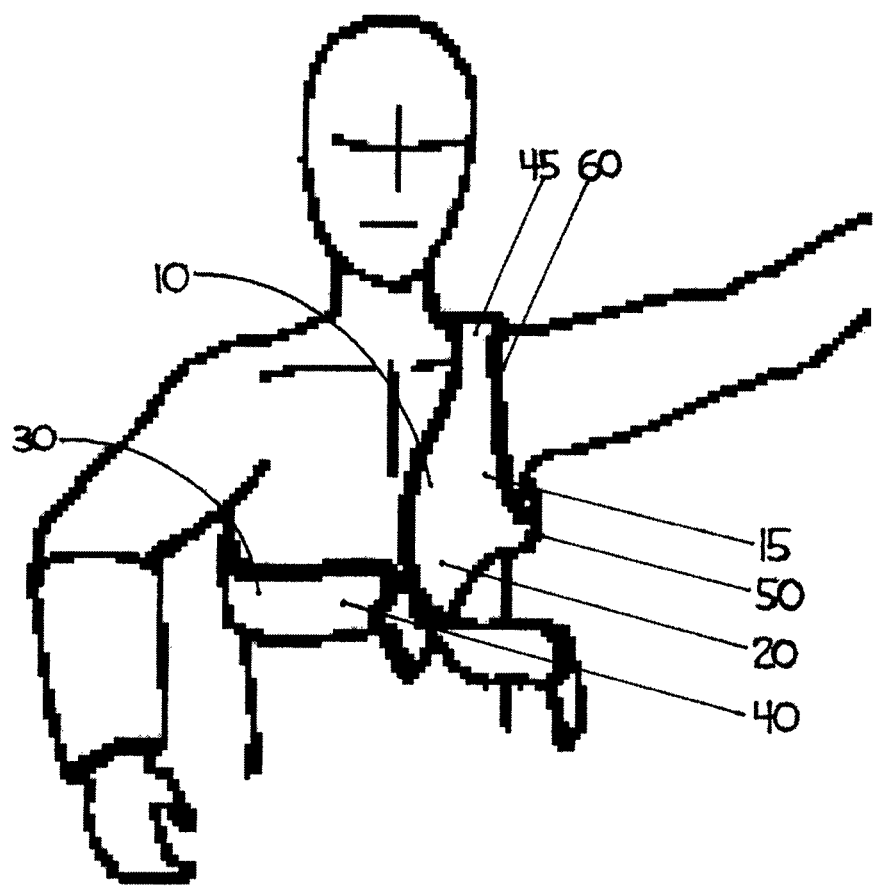
FIG. 3 is an illustration of a front view of an exemplary embodiment of the present invention.
Figure 4:
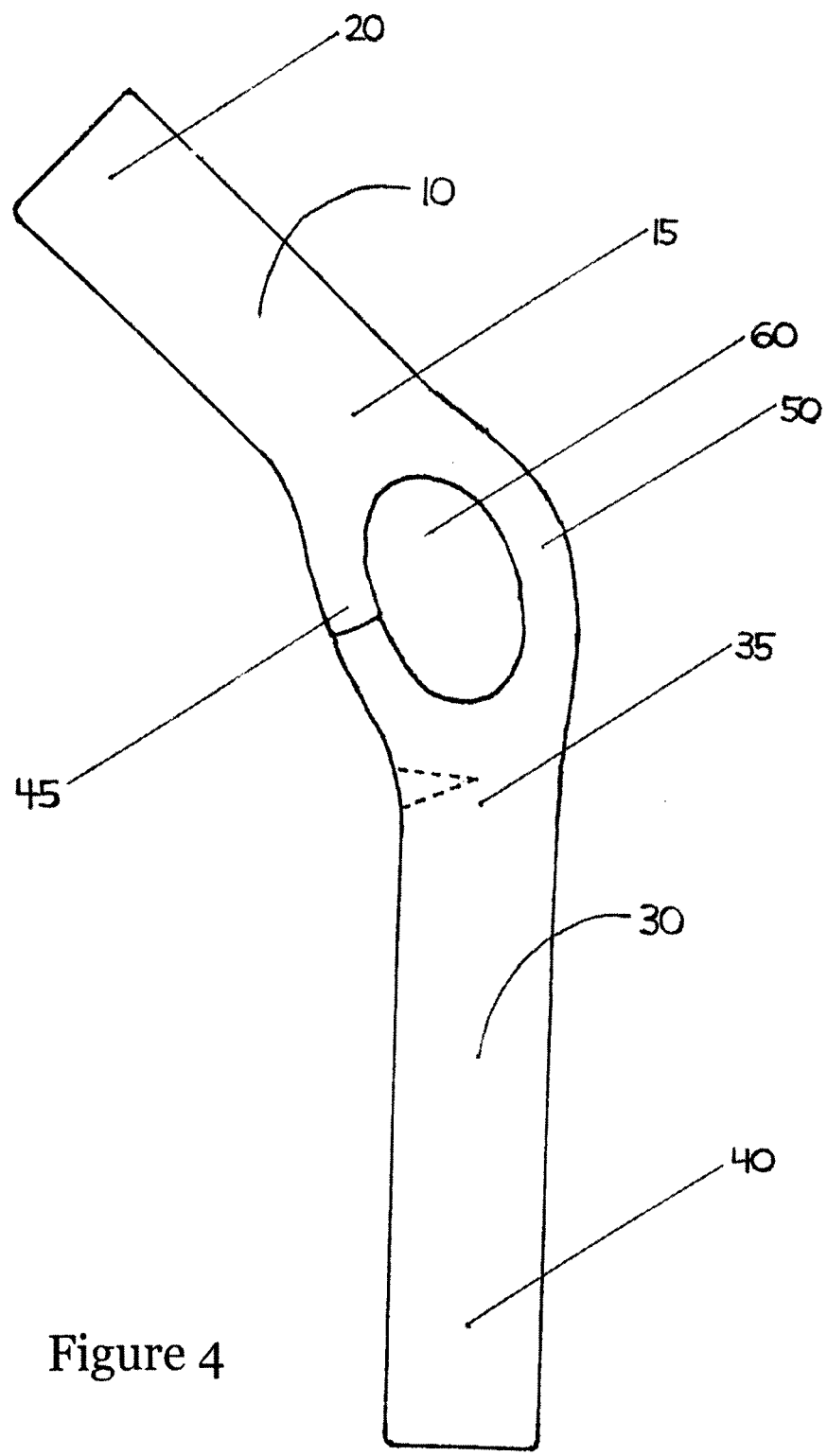
FIG. 4 is an illustration of a top view of an exemplary embodiment of the present invention.

The upper strip 45 and the lower strip 50 are also connected to a back strip 30 (see FIG. 3) at the higher part of said back strip 35 (see FIG. 4). In a preferred embodiment, the upper strip 45 and the lower strip 50, along with the higher part of said front strip 15 and the higher part of said back strip 35, define an opening 60 through which the unaffected arm is placed. In an exemplary embodiment, the front strip 10 and the back strip 30 are different lengths, and the width of the front strip 10 is substantially similar to the width of the back strip 30. The back strip 30 can also be viewed in FIGS. 2 and 4. In another embodiment, the upper strip 45 is detachably bisected (see FIG. 4) such that the unaffected arm can be placed in the opening 60, and the upper strip 45 can be reattached around the unaffected arm.

In the exemplary embodiment in which the upper strip 45 is detachably bisected, the upper strip may be held together via one or more securing means including, for example, hook and fastener strips, buttons, snaps, buckles, hooks, or a combination thereof.

Also displayed in FIG. 4, where the sling is laid out flat, are two ends of the sling, a base part of said front strip 20 and a base part of said back strip 40. These two ends are connected to each other around the torso, substantially on the side of the affected arm. This connection can be viewed in FIG. 3, another front view of the sling which displays the two ends connected to each other. Said base part of said front strip 20 and said base part of said back strip 40 are connected by a first connecting means, which could be hook and fastener strips, buttons, snaps, buckles, or hooks.

Figure 6:
FIG. 6 is an illustration of a side view of a pouch of an exemplary embodiment of the present invention.

FIG. 1 also displays a pouch 70 and an accompanying pouch strap 80. In a preferred embodiment, an anterior side of said pouch 70 and a posterior side of said pouch 70 are connected together such that the affected arm can be placed through open ends of said pouch 70, as viewed in FIG. 6. Further, said pouch strap 80 is connected at one end to said anterior side of said pouch 70 and at another end to said posterior side of said pouch 70 such that said pouch strap 80 is capable of supporting an elbow of the affected arm.

Figure 5:
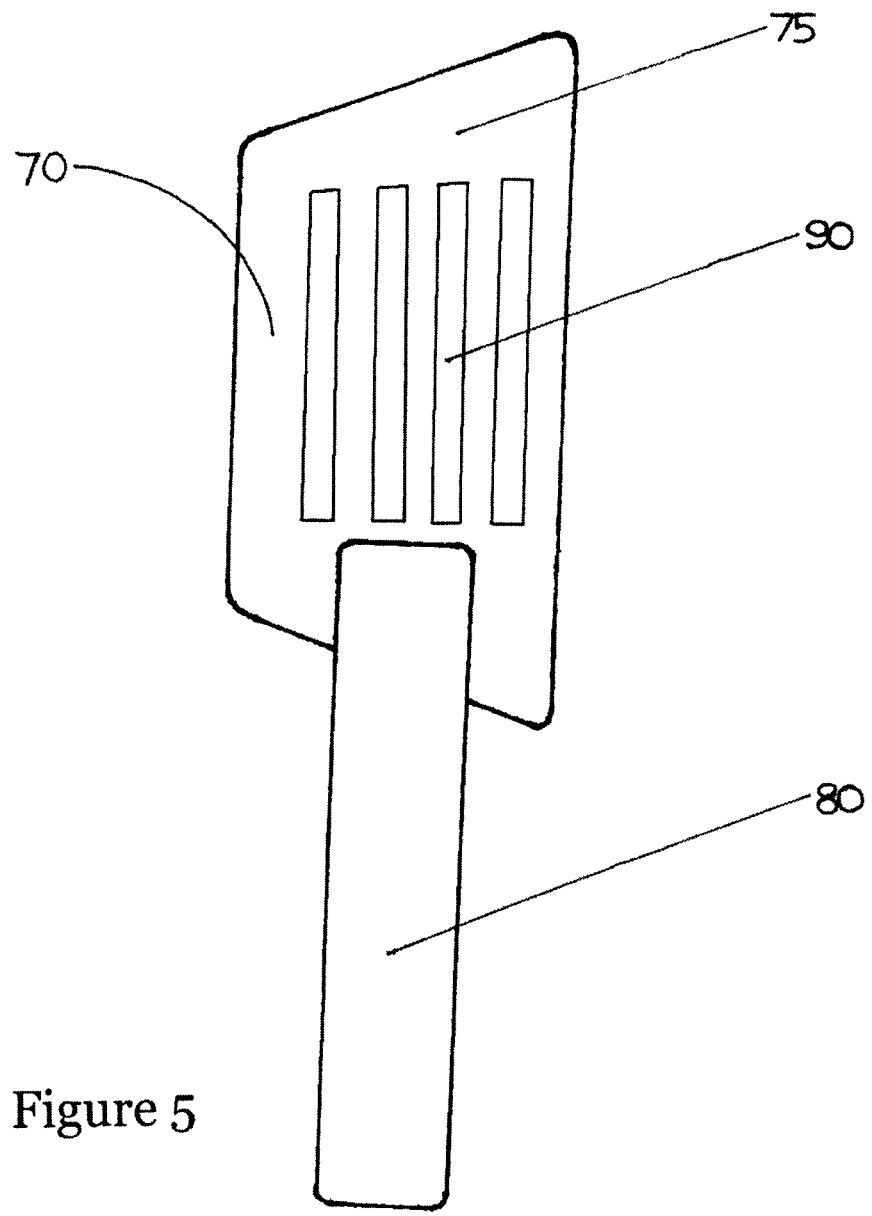
FIG. 5 is an illustration of a front view of a pouch of an exemplary embodiment of the present invention.

In an exemplary embodiment, an exterior side 75 of said pouch 70 can be attached to said front strip 10 by a second connecting means. This second connecting means can be hook and fastener strips, snaps, buckles, or hooks. This connection can be seen in FIGS. 1 and 2. In a preferred embodiment, the second connecting means are hook and fastener strips go, and FIGS. 1 and 5 show said pouch 70 and said exterior side 75 with said hook and fastener strips go. Said pouch 70, said exterior side 75, and said pouch strap 80, and said hook and fastener strips go are shown apart from the rest of the sling in FIG. 5. Said pouch 70 is otherwise unconnected to said front strip 10, said back strip 30, said upper strip 45, or said lower strip 50, and substantially covers and supports a forearm of said affected arm.

The sling can be made from any standard material used for slings such as cloth and certain parts of the sling may comprise of an elastic material.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:
1. A sling adapted to support a human arm comprising:
   a front strip having a higher part and a base part and capable of extending across a front of a torso,
   a back strip having a higher part and a base part and capable of extending across a back of a person, wherein said base part of said back strip is capable of connecting with said base part of said front strip by a first connecting means under a shoulder connected to an affected arm,
   an upper strip connecting a first portion of said higher part of said front strip and a first portion of said higher part of said back strip and supported by a shoulder connected to an unaffected arm,
   a lower strip connecting both a second portion of said higher part of said front strip and a second portion of said higher part of said back strip and supported by a side of a torso under said shoulder connected to said unaffected arm, wherein said lower strip defines an opening along with said higher part of front strip, said higher part of back strip, and said upper strip such that said unaffected arm can fit through, and
   a detachable pouch having an exterior side, an interior side, an anterior side, and a posterior side, wherein said exterior side of said pouch is capable of connecting with said front strip by a second connecting means, is otherwise unconnected to said front strip, said back strip, said upper strip, or said lower strip, and is adapted to substantially cover and support a forearm of said affected arm, wherein the shoulder of the affected arm and the person's neck do not directly assist the sling in supporting the affected arm.

2. The arm sling according to claim 1, wherein said front strip and said back strip have different lengths.

3. The arm sling according to claim 2, wherein a width of said front strip is substantially the same as a width of said back strip.

4. The arm sling according to claim 3, wherein said width of said front strip is less than the combined width of the said upper strip, said lower strip, and said opening.

5. The arm sling according to claim 1, wherein said anterior side of said pouch and said posterior side of said pouch are connected together such that a pouch opening exists at each end such that said forearm of said affected arm can fit through.

6. The arm sling according to claim 5, wherein a pouch strap is connected at one end to said anterior side of said pouch and at another end to said posterior side of said pouch such that said pouch strap is capable of supporting an elbow of said affected arm.

7. The arm sling according to claim 1, wherein said upper strip is detachable such that said upper strip can be unattached and reattached to place said unaffected arm into said opening.

8. The arm sling according to claim 1, wherein said arm sling is reversible.

9. The arm sling according to claim 1, wherein said first connecting means is selected from the group consisting of hooks and fasteners, snaps, buckles, and hooks.

10. The arm sling according to claim 1, wherein said second connecting means is selected from the group consisting of hooks and fasteners, snaps, buckles, and hooks.

11. A method for supporting an affected arm comprising the steps of:
   placing an unaffected arm through an opening on an arm sling, wherein said arm sling comprises a front strip having a higher part and a base part and capable of extending across a front of a torso, a back strip having a higher part and a base part and capable of extending across a back of a person, wherein said base part of said back strip is capable of connecting with said base part of said front strip by a first connecting means under a shoulder connected to said affected arm, an upper strip connecting a first portion of said higher part of said front strip and a first portion of said higher part of said back strip and supported by a shoulder connected to an unaffected arm, a lower strip connecting a second portion of said higher part of said front strip and a second portion of said higher part of said back strip and supported by a side of a torso under said shoulder connected to said unaffected arm, wherein said lower strip defines said opening along with said front strip, said back strip, and said upper strip such that said unaffected arm can fit through, and a detachable pouch having an exterior side and an interior side, wherein said exterior side of said pouch is capable of connecting with said front strip by a second connecting means, is otherwise unconnected to said front strip, said back strip, said upper strip, or said lower strip, and is adapted to substantially cover and support a forearm of said affected arm, wherein the shoulder of the affected arm and the person's neck do not directly assist the sling in supporting the affected arm,
   placing a forearm of said affected arm into said pouch, and connecting said exterior side of said pouch to said front strip such that said pouch is substantially supported.

12. The method for supporting an affected arm according to claim 11, wherein said front strip and said back strip have different lengths.

13. The method for supporting an affected arm according to claim 12, wherein a width of said front strip is substantially the same as a width of said back strip.

14. The method for supporting an affected arm according to claim 13, wherein said width of said front strip is less than the combined width of the said upper strip, said lower strip, and said opening.

15. The method for supporting an affected arm according to claim 11, wherein said anterior side of said pouch and said posterior side of said pouch are connected together such that a pouch opening exists at each end such that said forearm of said affected arm can fit through.

16. The method for supporting an affected arm according to claim 15, wherein a pouch strap is connected at one end to said anterior side of said pouch and at another end to said posterior side of said pouch such that said pouch strap is capable of supporting an elbow of said affected arm.

17. The method for supporting an affected arm according to claim 11, wherein said upper strip is detachable such that said upper strip can be unattached and reattached to place said unaffected arm into said opening.

18. The method for supporting an affected arm according to claim 11, wherein said arm sling is reversible.

19. The method for supporting an affected arm according to claim 11, wherein said first connecting means is selected from the group consisting of hooks and fasteners, snaps, buckles, and hooks.

20. The method for supporting an affected arm according to claim 11, wherein said second connecting means is selected from the group consisting of hooks and fasteners, snaps, buckles, and hooks.

\* \* \* \* \*